United States Patent

Yashiro et al.

[11] Patent Number: 6,043,355
[45] Date of Patent: Mar. 28, 2000

[54] PHTHALOCYANINE COMPOUNDS

[75] Inventors: Toru Yashiro, Kanagawa; Masatoshi Taniguchi, Kyoto-fu; Toshiro Narizuka, Kyoto-fu; Hiroaki Tomita, Kyoto-fu, all of Japan

[73] Assignees: Ricoh Company, Ltd., Tokyo; Yamada Chemical Co., Ltd., Kyoto, both of Japan

[21] Appl. No.: 09/017,703

[22] Filed: Feb. 5, 1998

[30] Foreign Application Priority Data

Aug. 4, 1997 [JP] Japan ................................. 9-221924

[51] Int. Cl.[7] .............................. C09B 47/18; C09B 67/12
[52] U.S. Cl. .......................... 540/139; 540/122; 540/140
[58] Field of Search ..................... 540/122, 139, 540/140

[56] References Cited

U.S. PATENT DOCUMENTS

| | | | |
|---|---|---|---|
| 5,169,745 | 12/1992 | Yashiro et al. | 430/495 |
| 5,238,722 | 8/1993 | Yashiro et al. | 428/64 |
| 5,242,730 | 9/1993 | Yashiro | 428/64 |
| 5,252,372 | 10/1993 | Yashiro et al. | 428/64 |
| 5,516,899 | 5/1996 | Campbell | 540/123 |
| 5,532,033 | 7/1996 | Yashiro | 428/64.1 |
| 5,580,696 | 12/1996 | Yashiro | 430/270.17 |
| 5,663,326 | 9/1997 | Wolleb | 540/139 |
| 5,830,267 | 11/1998 | Zambounis et al. | 106/413 |

FOREIGN PATENT DOCUMENTS

| | | |
|---|---|---|
| 0 272 565 | 6/1988 | European Pat. Off. . |
| 0272565 | 6/1988 | European Pat. Off. . |
| 0 491 951 | 7/1992 | European Pat. Off. . |
| 0 513 370 | 11/1992 | European Pat. Off. . |

OTHER PUBLICATIONS

Patent Abstracts of Japan, vol. 013, No. 156 (C–585), Apr. 14, 1989, & JP 63 312364 A (Daicel Chem Ind Ltd), Dec. 20, 1988 *abstract*.

Patent Abstracts of Japan, vol. 097, No. 002, Feb. 28, 1997, & JP 08 282110 A (Ricoh Co Ltd), Oct. 29, 1996 *abstract*.

Patent Abstracts of Japan, vol. 098, No. 002, Jan. 30, 1998, & JP 09 279050 A (Mitsubishi Chem Corp), Oct. 28, 1997 *abstract*.

*Primary Examiner*—Mukund J. Shah
*Assistant Examiner*—Pavanaram K Sripada
*Attorney, Agent, or Firm*—Oblon, Spivak, McClelland, Maier & Neustadt, P.C.

[57] ABSTRACT

A phthalocyanine compound of formula (I):

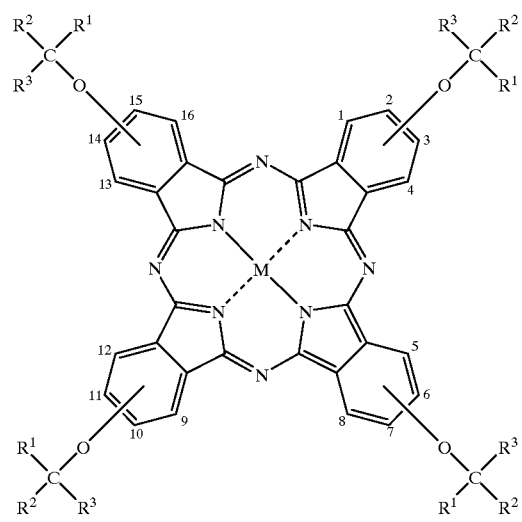

wherein FIGS. 1 to 16 around the phthalocyanine skeleton indicate the positions of carbon atoms in each benzene ring thereof; an oxygen atom is bonded to the carbon atom with position 1 or 4, to the carbon atom with position 5 or 8, to the carbon atom with position 9 or 12, and to the carbon atom with position 13 or 16; $R^1$ is a fluorine-atom substituted alkyl group; $R^2$ is an unsubstituted phenyl group or an alkyl-group-substituted phenyl group; $R^3$ is an unsubstituted alkyl group, a fluorine-atom substituted alkyl group or a hydrogen atom; and M represents Zn, Cu or Ni.

2 Claims, No Drawings

PHTHALOCYANINE COMPOUNDS

BACKGROUND OF THE INVENTION

1. Field of the Invention

The present invention relates to phthalocyanine compounds which can be employed as a dye for optical recording, a dye for color filter, and a material for use in photoelectric conversion device, electrophotographic photoconductor, organic semiconductor device, catalysts, gas sensor, and color filter.

2. Discussion of Background

Phathalocyanine compounds attract attention not only as conventionally employed pigments, but also as dyes for optical recording media, dyes for color filter, and materials for use in photoelectric conversion device, electrophotographic photoconductor, organic semiconductor device, catalysts, gas sensor, and color filter.

However, unsubstituted phthalocyanine compounds are slightly soluble or insoluble in most solvents and therefore considerably lack workability.

For instance, when a thin film of the unsubstituted phthalocyanine compound is formed for the above-mentioned applications, vacuum deposition or ultra fine particle dispersion method is generally employed. In either method, the productivity is extremely low. Thus, the slight solubility or insolubility in solvents of conventional phthalocyanine compounds is a great obstacle to the mass production of the above-mentioned media and devices.

In particular, when a phthalocyanine compound film prepared by vacuum deposition is used as a recording layer for an optical disk, it is necessary to perform crystal transformation of the recording layer into such a crystal form that is suitable for obtaining the recording characteristics required for the optical disk. This crystal transformation has to be conducted by heating the vacuum deposited phthalocyanine recording layer or exposing the vacuum deposited phthalocyanine recording layer to the vapor of an organic solvent for an extended period of time and the productivity of this method is significantly poor and therefore not used in practice for the production of optical disks.

With respect to optical disks, in particular, with compact disks, write once read many type compact disks have been actively developed in recent years. As organic dyes used as the materials for such write once read many type compact disks, cyanine dyes have been mainly used. Cyanine dyes are excellent in that they have large absorptivity coefficients, but have the shortcoming of not being light resistant. In order to eliminate this shortcoming, it has been proposed to add a photostabilizer such as a singlet oxygen quencher to the cyanine dyes. However, the addition of such a stabilizer is not sufficiently effective.

In sharp contrast to this, phthalocyanine dyes are comparable to the cyanine dyes and therefore the cyanine dyes can be replaced by phthalocyanine dyes with respect to the light absorption wavelength, and phthalocyanine dyes have high light resistance and therefore expected to find many applications in the field of recording materials. However, for such applications, the problem of phthalocyanine dyes that the solubilities thereof in organic solvents are extremely low has to be solved.

In order to solve this problem, it has been proposed to introduce some substituents into a phthalocyanine compound to improve the solubility thereof in organic solvents and use the phthalocyanine compound in the form of a coating liquid by dissolving the phthalocyanine compound in a solvent. For instance, in Japanese Laid-Open Patent Applications 1-180865, 2-265788 and 63-312888, there are disclosed phthalocyanine compounds with improved solubilities in organic solvents such as hydrocarbons with the introduction of an alkyl group, an alkoxyl group, or an alkylthio group in each benzene ring of phthalocyanine compounds.

Furthermore, it has been tried to introduce various functional groups such as ester group and polyether group into each benzene group of phthalocyanine dye compounds to increase the solubilities of phthalocyanine dye compounds in organic solvents.

However, when phthalocyanine compounds are used in a light absorption layer for an optical information recording medium, the phthalocyanine dye compounds have not only the problems of extremely low solubilities in organic solvents and poor workability, but also the problems that the absorptivity coefficients thereof on a longer wavelength side are lowered by the association of the molecules of the phthalocyanine dye compound in a superimposed manner when a film thereof is prepared because of the exceedingly high flatness of each phthalocyanine dye compound molecule, and that when used in write once read many type compact disks, with application of laser beams thereto, the recording sensitivity is not high due to the exceedingly high thermal stability of the phthalocyanine dye compounds.

The phthalocyanine dye compounds disclosed in the above-mentioned Japanese Patent Applications are improved with respect to the film formation properties, but the optical characteristics and thermal characteristics thereof are unsatisfactory and the above-mentioned problems have not yet been solved.

SUMMARY OF THE INVENTION

It is therefore an object of the present invention to provide a phthalocyanine compound free from the above-mentioned conventional shortcomings.

This object of the present invention can be achieved by a phthalocyanine compound of formula (I):

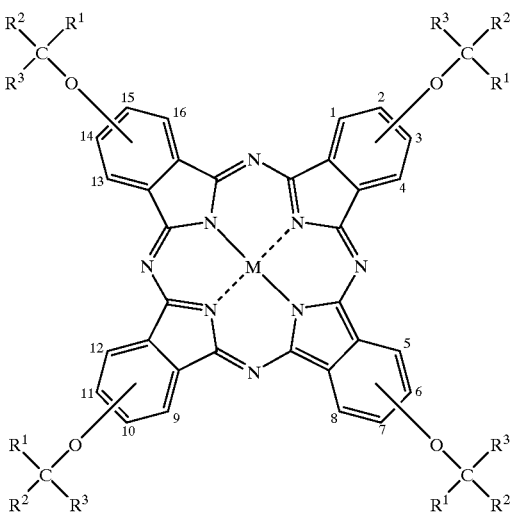

wherein FIGS. 1 to 16 around the phthalocyanine skeleton indicate the positions of carbon atoms in each benzene ring thereof; an oxygen atom is bonded to the carbon atom with position 1 or 4, to the carbon atom with position 5 or 8, to the carbon atom with position 9 or 12, and to the carbon atom with position 13 or 16; $R^1$ is a fluorine-atom substituted alkyl group; $R^2$ is an unsubstituted phenyl group or an alkyl-group-substituted phenyl group; $R^3$ is an unsubstituted alkyl group, a fluorine-atom substituted alkyl group or a hydrogen atom; and M represents Zn, Cu or Ni.

DESCRIPTION OF THE PREFERRED EMBODIMENTS

The phthalocyanine compound of the present invention is represented by formula (I):

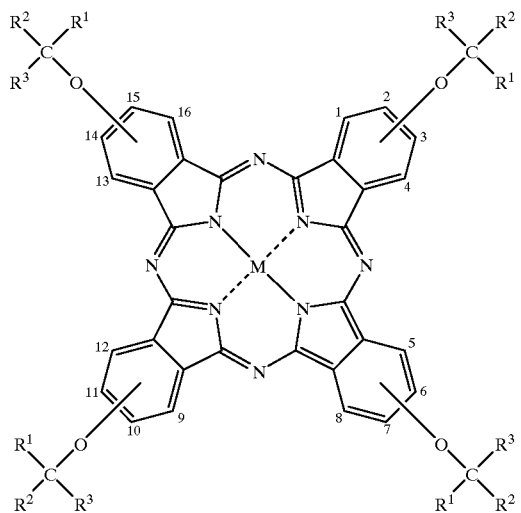

wherein FIGS. 1 to 16 around the phthalocyanine skeleton indicate the positions of carbon atoms in each benzene ring thereof; an oxygen atom is bonded to the carbon atom with position 1 or 4, to the carbon atom with position 5 or 8, to the carbon atom with position 9 or 12, and to the carbon atom with position 13 or 16; $R^1$ is a fluorine-atom substituted alkyl group; $R^2$ is an unsubstituted phenyl group or an alkyl-group-substituted phenyl group; $R^3$ is an unsubstituted alkyl group, a fluorine-atom substituted alkyl group or a hydrogen atom; and M represents zn, Cu or Ni.

In the phthalocyanine compound of the above formula (I), specific examples of the fluorine-atom substituted alkyl group represented by $R^1$ are trifluoromethyl group, pentafluoroethyl group, heptafluoro-n-propyl group, heptafluoro-iso-propyl group, and nonafluoro-n-butyl group.

Specific examples of the unsubstituted phenyl group or alkyl-group-substituted phenyl group represented by $R^2$ are phenyl group, 2-methylphenyl group, 4-methylphenyl group, 2,5-dimethylphenyl group, 2,4-dimethylphenyl group, 2,4,6-trimethylphenyl group, and 2,5-di-tert-butylphenyl group.

Specific examples of the unsubstituted alkyl group represented by $R^3$ are methyl group, ethyl group, n-propyl group, iso-propyl group, and straight-chain or branched butyl group, pentyl group, hexyl group, heptyl group and octyl group.

Specific examples of the fluorine-atom substituted alkyl group represented by $R^3$ are the same as those in the description of $R^1$.

The phthalocyanine compound of formula (I) of the present invention can be synthesized by allowing a phthalonitrile derivative, which is synthesized in accordance with a procedure as will be explained later, to react with a necessary metal salt in the presence of a strong organic base such as 1,8-diazabicyclo[5.4.0]-7-undecene (DBU) or 1,5-diazabicyclo[4.3.0]-5-nonene (DBN), in an alcohol solvent such as methanol, ethanol or n-pentanol.

The thus obtained phthalocyanine compound is highly soluble in various organic solvents such as hydrocarbon solvents, ether solvents, ketone solvents, ester solvents, alcohol solvents, and aromatic solvents, assuming a blue green or green color when dissolved in these solvents.

By spin-coating a solution of the phthalocyanine compound using any of the above solvents, for instance, on a polycarbonate substrate, a uniform thin layer of the phthalocyanine compound can be formed.

The thus prepared thin layer of the phthalocyanine compound does not exhibit a decreased absorptivity coefficient in a visible wavelength area, unlike thin layers of conventional phthalocyanine compounds, so that the thin layer of the phthalocyanine compound according to the present invention is suitable for the application of an optical information recording medium.

In the phthalocyanine compound of the present invention, the phenyl group or fluorine-atom substituted alkyl group is bulky, so that the association of the molecules of the phthalocyanine compound, which causes a significant reduction in absorptivity coefficient, is effectively hindered.

It is considered that the above-mentioned preferable absorption spectrum characteristics of the phthalocyanine compound of the present invention are available due to the above-mentioned hindering of the association of the molecules of the phthalocyanine compound.

Further, with respect to the thermal characteristics of the phthalocyanine compound, a moiety of the phenyl-methyloxy group, which is contained in the phthalocyanine compound of the present invention, is generally considered to have an easily thermally decomposable structure. As a matter of fact, the phthalocyanine compound represented by formula (I) of the present invention is exothermically decomposed at temperatures in the range of 200° C. to 400° C., so that the phthalocyanine compound of the present invention is suitable as the material for write once read many type compact disks.

Furthermore, the fluorine-atom substituted alkyl group contained in the phthalocyanine compound of the present invention imparts sufficient light stability and thermal stability, which are desirable for the application of the recording material, to the obtained phthalocyanine compound.

The overall characteristics of the molecule of the phthalocyanine compound of the present invention can be flexibly controlled with the balance between the abovementioned characteristic atoms and substituents being taken into consideration. Thus, the phthalocyanine compound of the present invention has high adaptability to the optical recording material which requires delicate adjustments to the characteristics of the molecule of the phthalocyanine compound.

The phthalonitrile derivative with a fluorine-containing substituent, which is necessary for the synthesis of the phthalocyanine compound of the present invention, can be prepared by allowing a fluorine-containing benzyl alcohol derivative, which can be synthesized by any of the following methods (a), (b), (c), (d), and (e), to react with 3-nitrophthalonitrile:

(a) a benzene derivative is allowed to react with a fluorine-containing carboxylic anhydride or a fluorine-containing halogenated carboxylic acid by Friedel-Crafts reaction to prepare a fluorine-containing acetophenone derivative, and the thus prepared fluorine-containing acetophenone derivative is reduced.

(b) a benzene derivative and a fluorine-containing acetone derivative are subjected to Friedel-Crafts reaction.

(c) a halogenated benzoyl derivative is allowed to react with a fluorine-containing unsaturated hydrocarbon in the presence of a fluoride ion to prepare a fluorine-containing acetophenone derivative, and the thus prepared fluorine-containing acetophenone derivative is reduced.

(d) an organic metallic compound such as phenyl lithium or phenyl magnesium bromide is allowed to react with a fluorine-containing carbonate to prepare a fluorine-containing acetophenone derivative, and the thus prepared fluorine-containing acetophenone derivative is reduced.

(e) a benzaldehyde derivative is allowed to react with a fluorine-containing alkyl halide in the presence of metallic zinc.

Other features of this invention will become apparent in the course of the following description of exemplary embodiments, which are given for illustration of the invention and are not intended to be limiting thereof.

EXAMPLE 1

Synthesis of Phthalocyanine Compound No. 1 in TABLE 1

Step (1-1) (Synthesis of benzyl alcohol derivative of 1-phenyl-2,2,2-trifluoroethanol)

5.0 q of 2,2,2-trifluoroacetophenone (available from Tokyo Kasei Kogyo Co., Ltd.), 11.8 g of aluminum triisopropoxide, and 100 ml of isopropyl alcohol were placed in a flask equipped with a reflux condenser. This reaction mixture was heated with stirring to a refluxing temperature thereof and refluxed with stirring for 1.5 hours.

This reaction mixture was then allowed to stand at room temperature and cooled to room temperature. The reaction mixture was then poured into 1000 ml of iced water, and the pH of the mixture was adjusted to 3 with the addition of a 20% aqueous solution of hydrochloric acid thereto.

The above reaction mixture was extracted with 200 ml of toluene. The toluene extract layer was separated from the mixture and dried over magnesium sulfate. Toluene was distilled away from the toluene extract layer, whereby a benzyl alcohol was obtained as the residue in a yield of 5.1 g.

The analysis data of the thus obtained benzyl alcohol was as follows:

| Mass spectrum: | 176 (M$^+$) |
|---|---|
| IR spectrum: | 3500 cm$^{-1}$ (vOH) |
| | 1120 to 1170 cm$^{-1}$(vCF) |

Step (1-2) (Synthesis of phthalonitrile derivative)

5.0 g of the benzyl alcohol derivative obtained in the above Step (1-1), 7.9 g of anhydrous potassium carbonate, 30 ml of dimethyl sulfoxide, and 4.5 g of 3-nitrophthalonitrile were placed in a flask.

This reaction mixture was stirred in a stream of nitrogen at 70° C. for 4 hours and then poured into 1000 ml of water. Crystals which separated out in the mixture were filtered off and dried, whereby a phthalonitrile derivative was obtained in a yield of 6 g.

The analysis data of the thus obtained phthalonitrile derivative was as follows:

| Mass spectrum: | 302 (M$^+$) |
|---|---|
| IR spectrum (KBr): | 2230 cm$^{-1}$ (vCN), |
| | 1140 to 1180 cm$^{-1}$(vCF) |
| Melting point: | 165 to 167° C. |

Step (1-3) (Synthesis of phthalocyanine compound No. 1 in TABLE 1)

5.0 g of the phthalonitrile derivative prepared in the above Step (1-2), 4.5 g of 1,8-diazabicyclo[5.4.0]-7-undecene (hereinafter referred to as DBU), 33 ml of 1-pentanol, and 0.64 g of zinc chloride were placed in a flask.

This reaction mixture was stirred in a stream of nitrogen at 100° C. for 5 hours.

This reaction mixture was then poured into 100 ml of methanol. To this mixture, 20 ml of water was further added. Crystals which separated out in the mixture were filtered off and dried, whereby a crude product of a phthalocyanine compound No. 1 was obtained in a yield of 4.4 g.

3 g of this crude product was chromatographed on silica gel and eluted with a mixed solvent of toluene and ethyl acetate (20:1), whereby 1.6 g of a purified phthalocyanine compound No. 1 was obtained.

The analysis data of the thus obtained phthalocyanine compound No. 1 was as follows:

| IR spectrum (KBr): | 1110 to 1180 cm$^{-1}$(vCF) |
|---|---|
| Solubility in 1,2-dichloroethane: | 2% or more at room temperature |
| Solubility in toluene: | 2% or more at room temperature |
| Solubility in ethyl cellosolve: | 2% or more at room temperature |
| DSC analysis: | Exothermic peaks near 247° C. |
| TG analysis: | Reduction in weight began to be observed near 240° C. |

The result of the elemental analysis of the phthalocyanine compound No. 1 was as follows:

| | % C | % H | % N |
|---|---|---|---|
| Found | 60.48 | 2.90 | 8.66 |
| Calculated | 60.32 | 2.85 | 8.79 |

The calculation is based on the formula for $C_{54}H_{26}N_8O_4F_{12}Zn$.

EXAMPLE 2

Synthesis of Phthaloacyanine Compound No. 2 in TABLE 1

Step (2-1) (Synthesis of acetophenone derivative of 2,2,3,3-pentafluoro-1-phenylpropanone)

25 g of methyl pentafluoropropionate and 630 ml of anhydrous ethyl ether were placed in a flask equipped with a reflux condenser. This reaction mixture was cooled using dry ice and acetone. When the reaction mixture was cooled to temperature in the range of −45 to −60° C., 78 ml of phenyl lithium was added dropwise to the reaction mixture over a period of 30 minutes, and then the reaction mixture was stirred for one hour with the temperature being maintained at −45° C. or less. Thereafter, the reaction mixture was further stirred for 2.5 hours as being allowed to stand at room temperature.

When the reaction mixture was returned to room temperature, the reaction mixture was poured into 1000 ml of a 7% aqueous solution of hydrochloric acid, and the resultant ether layer was separated from the reaction mixture. The ether layer was successively washed with 1000 ml of a 5% aqueous solution of sodium carbonate, and 1000 ml of an aqueous solution of sodium chloride, and dried over magnesium sulfate. Magnesium sulfate was removed from the mixture by filtration, and then the ether was distilled away from the resulting filtrate, whereby 22 g of an acetophenone derivative was obtained as a light brown-yellow oily material.

The analysis data of the thus obtained acetophenone derivative was as follows:

| | |
|---|---|
| Mass spectrum: | 224 (M$^+$) |
| IR spectrum: | 1709 cm$^{-1}$ (vCO) |
| | 1100 to 1217 cm$^{-1}$(vCF) |

Step (1-2) (Synthesis of benzyl alcohol derivative of 2,2,3,3,3-pentafluoro-1-phenylpropanol)

22 g of the acetophenone derivative obtained in the above step (1-1) and 300 ml of isopropyl alcohol were placed in a flask . This reaction mixture was heated to 40° C. with stirring. 15 g of sodium boron hydroxide was added to the reaction mixture, and the mixture was further stirred at 40° C. for 3.5 hours.

This reaction mixture was then allowed to stand at room temperature and cooled to room temperature. The reaction mixture was then poured into 1500 ml of water, and extracted with diethyl ether. The extract layer was washed with water and dried over magnesium sulfate, and then concentrated , whereby a benzyl alcohol derivative was obtained as a light brown oily material in a yield of 19 g.

The analysis data of the thus obtained benzyl alcohol was a follows:

| | |
|---|---|
| Mass spectrum: | 226 (M$^+$) |
| IR spectrum: | no absorption peak (vCO) |
| | 3360 cm$^{-1}$(vOH) |
| | 1130 to 1210 cm$^{-1}$(vCF) |

Step (1-3) (Synthesis of phthalonitrile derivative)

19 g of the benzyl alcohol derivative obtained in the above Step (1-2), 9.4 g of anhydrous potassium carbonate, and 50 ml of dimethyl sulfoxide were placed in a flask. A solution prepared by dissolving 5.9 g of 3-nitrophthalonitrile in 20 ml of dimethyl sulfoxide was added dropwise to the reaction mixture at 45° C. with stirring over a period of one hour.

After this reaction mixture was stirred at 60° C. for 4 hours, the reaction mixture was poured into 600 ml of water and extracted with ethyl acetate. The resultant extract layer was washed with water, and ethyl acetate was distilled away from the extract layer. Thus, a phthalonitrile derivative was obtained as a light brown oily material in a yield of 8 g.

The analysis data of the thus obtained phthalonitrile derivative was as follows:

| | |
|---|---|
| Mass spectrum: | 352 (M$^+$) |

Step (1-4) (Synthesis of phthalocyanine compound No. 2 in TABLE 1)

8 g of the phthalonitrile derivative obtained in the above Step (1-3), 6.0 g of DBU, and 25 ml of 1-pentanol were placed in a flask. The reaction mixture was heated to 90° C. with stirring in a stream of nitrogen. With the addition of 0.45 g of zinc chloride, the reaction mixture was stirred at 100° C. for 6 hours.

This reaction mixture was then allowed to stand at room temperature and poured into 200 ml of methanol. To this mixture, 100 ml of water was further added. Crystals which separated out in the mixture were filtered off and dried, whereby a crude product of a phthalocyanine compound No. 2 was obtained in a yield of 6.9 g.

This crude product was chromatographed on silica gel and eluted with a mixed solvent of toluene and ethyl acetate (40;1), whereby 2.5 g of a purified phthalocyanine compound No. 2 was obtained.

The analysis data of the thus obtained phthalocyanine compound No. 2 was as follows;

| | |
|---|---|
| Solubility in ethyl cellosolve: | 2% more at room temperature |
| DSC analysis: | Exothermic peaks near 215° C. and 373° C. |
| TG analysis: | Reduction in weight began to be observed near 200° C. |

EXAMPLE 3

Synthesis of Phthalocyanine Compound No. 3 in TABLE 1

Step (1-1) (Synthesis of phthalonitrile derivative)

10 g of 1,1,1,3,3,3-hexafluoro-2-phenyl-2-propanol (available from Central Glass Co., Ltd.), 16 g of anhydrous potassium carbonate, and 25 ml of N,N-dimethylformamide were placed in a flask. 4.8 g of 3-nitrophthalonitrile was added dropwise to the above reaction mixture over a period of 40 minutes with stirring with the temperature of the reaction mixture being maintained in the range of 40 to 50° C.

This reaction mixture was stirred at 70° C. for 6 hours and then poured into 600 ml of water. Crystals which separated out in the mixture were filtered off and dried, whereby a phthalonitrile derivative was obtained in a yield of 5.2 g.

The analysis data of the thus obtained phthalonitrile derivative was as follows:

| | |
|---|---|
| Mass spectrum: | 370 (M$^+$) |
| Melting point: | 150 to 152° C. |

Step (1-2) (Synthesis of phthalocyanine compound No. 3 in TABLE 1)

5.2 g of the phthalonitrile derivative obtained in the above Step (1-1), 5.1 g of DBU, 30 ml of 1-pentanol, and 0.64 g of zinc chloride were placed in a flask.

This reaction mixture was stirred in a stream of nitrogen at temperature in the range of 90 to 95° C. for 5 hours.

This reaction mixture was then poured into 300 ml of methanol. To this mixture, 100 ml of water was further added. Crystals which separated out in the mixture were filtered off and dried, whereby a crude product of a phthalocyanine compound No. 3 was obtained in a yield of 5.3 g.

This crude product was chromatographed on silica gel and eluted with toluene, whereby 2.0 g of a purified phthalocyanine compound No. 3 was obtained.

The analysis data of the thus obtained phthalocyanine compound No. 3 was as follows:

| | |
|---|---|
| Solubilities in tetrahydrofuran, acetone, ethanol, ethyl acetate and toluene: | 1% or more at room temperature |
| DSC analysis: | Exothermic peaks near 245° C. |
| TG analysis: | Reduction in weight began to be observed near 230° C. |
| IR spectrum (KBr): | 1110 to 1150 cm$^{-1}$(vCF) |
| ιH-NHR (tetrahydrofuran): | δ (ppm from TMS) 7.1–7.5 (8H,m), 7.6–8.1 (20H,m), c9.2–9.4 (4H,m) |

EXAMPLE 4

Synthesis of Phthalocyanine Compound No. 4 in TABLE 1

Step (1-1) (Synthesis of benzyl alcohol derivative of 2,2,3,3,4,4,5,5,5-nonafluoro-1-phenylpentanol)

7.5 g of benzaldehyde, 175 ml of dimethylformamide, and 11 g of zinc powder were placed in a flask. This reaction mixture was maintained at room temperature on a water bath, and irradiated by ultrasonic wave of 45 kHz. 29.5 g of nonafluorobutyl iodide was added dropwise to the reaction mixture over a period of 30 minutes.

After the reaction mixture was further irradiated by ultrasonic wave for 4 hours with the temperature thereof being maintained at 20 to 30° C., the reaction mixture was poured into 1000 ml of a 5% aqueous solution of hydrochloric acid.

200 ml of toluene was added to the reaction mixture, and zinc powder was removed from the reaction mixture by filtration. The resultant toluene layer was separated from the filtrate, and successively washed with a 2% aqueous solution of sodium carbonate and water, and then toluene was distilled away, whereby a benzyl alcohol was obtained as a light brown oily material in a yield of 4 g.

The analysis data of the thus obtained benzyl alcohol was as follows:

| | |
|---|---|
| Mass spectrum: | 326 (M$^+$) |
| IR spectrum: | 3450 cm$^{-1}$ (vOH) 1140 to 1350 cm$^{-1}$(vCF) |

Step (1-2) (Synthesis of phthalonitrile derivative)

4 g of the benzyl alcohol derivative obtained in the above Step (1-1), 5.5 g of anhydrous potassium carbonate, 1.7 g of 3-nitrophthalonitrile, and 20 ml of dimethyl sulfoxide were placed in a flask.

This reaction mixture was stirred at temperature in the range of 50 to 60° C. for 3 hours, and then allowed to stand at room temperature. Thereafter, the reaction mixture was poured into 500 ml of water. Crystals which separated out in the mixture were filtered off and dried, whereby a phthalonitrile derivative was obtained as a light brown solid in a yield of 3.5 g.

The analysis data of the thus obtained phthalonitrile derivative was as follows:

| | |
|---|---|
| Mass spectrum: | 452 (M$^+$) |
| IR spectrum (KBr): | 2230 cm$^{-1}$(vCN), 1130 to 1350 cm$^{-1}$(vCF) |
| Melting point: | 100 to 110° C. |

Step (1-3) (Synthesis of phthalocyanine compound No. 4 in TABLE 1)

3.5 g of the phthalonitrile derivative obtained in the above Step (1-2), 20 ml of 1-pentanol, and 0.35 g of zinc chloride were placed in a flask.

This reaction mixture was heated to 90° C. with stirring in a stream of nitrogen, and 3.6 g of DBU was added dropwise to the reaction mixture over a period of 30 minutes.

After the completion of addition of DBU, this reaction mixture was stirred at 95° C. for 6 hours.

Thereafter, the reaction mixture was allowed to stand at room temperature and poured into 200 ml of methanol. To this mixture, 100 ml of water was further added. Crystals which separated out in the mixture were filtered off and dried, whereby a crude product of a phthalocyanine compound No. 4 was obtained in a yield of 3.1 g.

This crude product was chromatographed on silica gel and eluted with toluene, whereby 0.4 g of a purified phthalocyanine compound No. 4 was obtained.

The analysis data of the thus obtained phthalocyanine compound No. 4 was as follows:

| | |
|---|---|
| Solubility in ethyl cellosolve: | 1% or more at room temperature |
| Solubility in 1,2-dichloroethane: | 1% or more at room temperature |

EXAMPLE 5

Synthesis of Phthalocyanine Compound No. 5 in TABLE 1

The procedure for synthesis of the phthalocyanine compound No. 3 in Example 3 was repeated except that zinc chloride in an amount of 0.64 g used in the step (1-2) in Example 3 was replaced by cuprous chloride. Thus, a purified phthalocyanine compound No. 5 was obtained in a yield of 2.5 g.

The analysis data of the thus obtained phthalocyanine compound No. 5 was as follows:

| | |
|---|---|
| Solubility in tetrahydrofuran; | 1% or more at room temperature |
| DSC analysis: | Exothermic peaks near 233 to 265° C. |
| TG analysis: | Reduction in weight began to be observed near 220° C. |

EXAMPLE 6

Synthesis of Phthalocyanine Compound No. 6 in TABLE 1

The procedure for synthesis of the phthalocyanine compound No. 1 in Example 1 was repeated except that zinc chloride in an amount of 0.64 g used in the step (1-3) in Example 1 was replaced by nickel chloride. Thus, a purified phthalocyanine compound No. 6 was obtained in a yield of 0.8 g.

The analysis data of the thus obtained phthalocyanine compound No. 6 was as follows:

| Solubility in 1,2-dichloroethane: | 1% or more at room temperature |
|---|---|

Reference Example 1

Synthesis of Reference Phthalocyanine Compound No. 7 in TABLE 1

The procedure for synthesis of the phthalocyanine compound No. 5 in Example 5 was repeated except that cuprous chloride in an amount of 0.64 g used in Example 5 was replaced by vanadium trichloride. Thus, a reference phthalocyanine compound No. 7 was obtained.

TABLE 1 shows the substituent (-O-CR$^1$R$^2$R$^3$), the central metal and the absorption maximum wavelength ($\lambda_{max}$) of the absorption spectrum in tetrahydrofuran of each phthalocyanine compound synthesized in Examples 1 to 6 and Reference Example 1.

TABLE 1

| | Compound No. | Substituent (—O—CR$^1$R$^2$R$^3$) | Central Metal M | λmax (nm) |
|---|---|---|---|---|
| Ex. 1 | 1 | —O—CH(CF$_3$)(C$_6$H$_5$) | Zn | 690 |
| Ex. 2 | 2 | —O—CH(C$_2$F$_3$)(C$_6$H$_5$) | Zn | 689 |
| Ex. 3 | 3 | —O—C(CF$_3$)$_2$(C$_6$H$_5$) | Zn | 685 |
| Ex. 4 | 4 | —O—CH(C$_4$F$_9$)(C$_6$H$_5$) | Zn | 686 |
| Ex. 5 | 5 | —O—C(CF$_3$)$_2$(C$_6$H$_5$) | Cu | 687 |
| Ex. 6 | 6 | —O—CH(CF$_3$)(C$_6$H$_5$) | Ni | 688 |
| Reference Ex. 1 | 7 | —O—C(CF$_3$)$_2$(C$_6$H$_5$) | VO | 718 |

Application Example

Fabrication of Optical Recording Medium

A pattern of guide groove with a depth of about 1500 Å was formed on the surface of a polycarbonate substrate with a diameter of 120 mm and a thickness of 1.2 mm.

A coating liquid for a light absorption layer was prepared by mixing the phthalocyanine compound No. 3 in TABLE 1 and the phthalocyanine compound No. 7 serving as a sensitizer in the ratio by weight of 3:2, and the thus prepared mixture was dissolved in a mixed solvent of tetrahydrofuran, 1-methoxy-2-butanol and ethyl cyclohexane. The coating liquid thus prepared was applied to the polycarbonate substrate by spin-coating, so that the light absorption layer was provided on the polycarbonate substrate.

The absorption maximum wavelength ($\lambda_{max}$) of the light absorption layer thus obtained was 710 nm, and the thickness of the light absorption layer was about 1500 Å.

A light reflection layer with a thickness of about 1000 Å was provided on the light absorption layer by sputtering of Au.

Further, there was provided on the light reflection layer a 5-μm-thick protective layer comprising an ultraviolet-curing resin (Trademark SD-1700", made by Dainippon Ink & Chemicals, Incorporated).

Thus, a write once read many type compact disk was fabricated.

Information was recorded in the thus fabricated compact disk using a commercially available CD-writer (Trademark CDW-900E, made by Sony Corporation) at a 2×nominal CD speed, and the recorded information was reproduced using a commercially available CD player (Trademark CDP-M51/2, made by Sony Corporation). In this reproduction test, the reproducing operation was normally carried out. In addition, the number of C1 errors decoded from the CD player was 50 or less, which satisfied the CD standard (220 or less).

As previously explained, the phthalocyanine compound of the present invention is readily soluble in a variety of organic solvents at room temperature, so that this phthalocyanine compound shows excellent workability when formed into a thin film. In addition, since the film of the phthalocyanine compound exhibits high absorptivity coefficient and excellent thermal response performance, the phthalocyanine compound of the present invention can be used in various applications, for example, as the optical recording material.

Japanese Patent Application No. 09-221924 filed Aug. 4, 1997 is hereby incorporated by reference.

What is claimed is:

1. A phthalocyanine compound of formula (I):

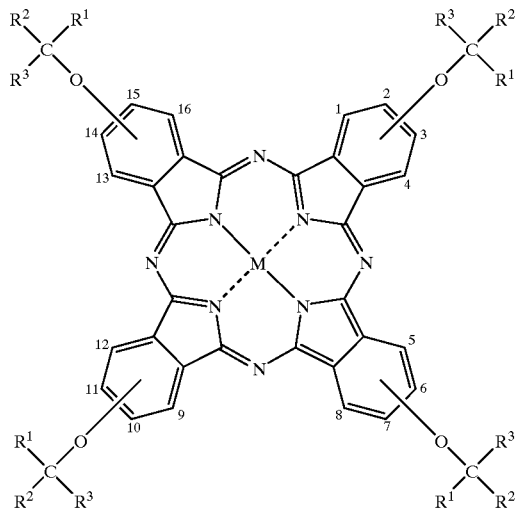

wherein FIGS. 1 to 16 around the phthalocyanine skeleton indicate the positions of carbon atoms in each benzene ring thereof; an oxygen atom is bonded to the carbon atom with position 1 or 4, to the carbon atom with position 5 or 8, to the carbon atom with position 9 or 12, and to the carbon atom with position 13 or 16; $R^1$ is a fluorine-atom substituted alkyl group; $R^2$ is an unsubstituted phenyl group or an alkyl-group-substituted phenyl group; $R^3$ is an unsubstituted alkyl group, a fluorine-atom substituted alkyl group or a hydrogen atom; and M represents Zn, Cu or Ni.

2. The phthalocyanine compound as claimed in claim 1, wherein $R^1$ is perfluoroalkyl group having 1 to 4 carbon atoms, $R^2$ is phenyl group, and R3 is trifluoromethyl group or hydrogen atom.

* * * * *